United States Patent [19]

Kasuga

[11] Patent Number: 4,871,384
[45] Date of Patent: Oct. 3, 1989

[54] PROCESS FOR SURFACE MODIFICATION OF INORGANIC BIOMATERIAL

[75] Inventor: Toshihiro Kasuga, Akishima, Japan

[73] Assignee: Hoya Corporation, Tokyo, Japan

[21] Appl. No.: 187,457

[22] Filed: Apr. 28, 1988

[30] Foreign Application Priority Data

Apr. 28, 1987 [JP]   Japan ................... 62-106068

[51] Int. Cl.[4] ............ C03C 10/00; C03C 10/06; C03C 10/04; C03C 21/00
[52] U.S. Cl. .................... 65/30.1; 65/33; 501/5; 501/8
[58] Field of Search ............ 65/30.1, 33, 60.5; 427/399; 501/5, 8, 10; 428/704

[56] References Cited

U.S. PATENT DOCUMENTS

| | | | |
|---|---|---|---|
| 3,460,967 | 8/1969 | Petticrew | 65/30.1 |
| 4,493,849 | 1/1985 | Carroll | 426/5 |
| 4,515,770 | 5/1985 | Besic | 426/72 |
| 4,652,534 | 3/1987 | Kasuga | 501/10 |
| 4,781,744 | 11/1988 | Kobayashi | 501/10 |
| 4,783,429 | 11/1988 | Shibuya | 501/5 |

OTHER PUBLICATIONS

*Treatise on Biomedical Materials*, "A New Bioactive Glass-Ceramic for Artificial Bone", Nakamura et al., Nov. 12, 1983, pp. 109–117.

*Primary Examiner*—Kenneth M. Schor
*Attorney, Agent, or Firm*—Nixon & Vanderhye

[57] ABSTRACT

According to the present process for modifying the surface of a biomaterial, there can be precipitated on the surface of a biomaterial a calcium phosphate crystal which is necessary for the biomaterial to form a chemical bonding with human bones. Therefore, the bioactivity of a biomaterial for use as an artifical bone or a dental implant can be improved by the present process.

6 Claims, 2 Drawing Sheets

PROCESS FOR SURFACE MODIFICATION OF INORGANIC BIOMATERIAL

BACKGROUND OF THE INVENTION

1. Field of the Invention

The present invention relates to a process for modifying the surface of an inorganic biomaterial and more particularly to a process for modifying the surface of an inorganic biomaterial which is useful as an implant material for artificial bones, dental implants, etc., to further improve the bioactivity of the biomaterial.

2. Description of Prior Art

As so-called bioactive ceramics capable of forming a chemical bonding with bones, there are known sintered apatite and a crystallized glass in the system of $Na_2O$-$K_2O$-$MgO$-$CaO$-$SiO_2$-$P_2O_5$. As the bioactive ceramic, there is further known a crystallized glass in the system of $MgO$-$CaO$-$P_2O_5$-$SiO_2$. This crystallized glass contains an apatite crystal and a wollastonite crystal, and the apatite crystal contributes to the bioactivity and the wollastonite crystal contributes to the mechanical strength. As to the bending strengths of these ceramics, the sintered apatite has about 1,000 to 1,400 kg/cm$^2$; the $Na_2O$-$K_2O$-$MgO$-$CaO$-$SiO_2$-$P_2O_5$ system crystallized glass about 1,000 to 1,500 kg/cm$^2$; the $MgO$-$CaO$-$P_2O_5$-$SiO_2$ system crystallized glass about 1,200 to 1,400 kg/cm$^2$.

A $CaO$-$P_2O_5$-$SiO_2$ system or $CaO$-$P_2O_5$-$SiO_2$-($MgO$, $Y_2O_3$) system crystallized glass containing a larger amount of a wollastonite crystal is also known, and it has a high bending strength of 1,700 to 2,300 kg/cm$^2$.

However, these bending strengths are not yet fully satisfactory from the standpoint that the above materials are used as an artificial bone or a dental implant. Hence, a biomaterial of higher strength is desired.

As biomaterials of higher strength, there are known composite sintered products consisting of a bioactive crystallized glass as mentioned above and a high strength ceramic powder (e.g. zirconia, alumina, or zirconia-alumina). These composites have a high bending strength of 2,500–3,800 kg/cm$^2$ which is comparable to that of sintered alumina.

The above ceramic-crystallized glass composites, however, have lower bioactivity to bones than crystallized glasses per se because in the composites the content of the crystallized glass capable of forming a chemical bonding with bones is reduced by the incorporation of the ceramic incapable of forming a chemical bonding with bones by itself. Therefore, it is desired to improve the bioactivity of the composites.

Crystallized glasses per se have poor bioactivity in some cases, depending upon their compositions. Therefore, it is also desired to improve the bioactivity of crystallized glasses having low bioactivity.

Hence, an object of the present invention is to improve a process for modifying the surface of an inorganic biomaterial such as a crystallized glass or a ceramic-crystallized glass composite in order to improve its bioactivity.

Other objects of the present invention will be apparent from the following descriptions and drawings.

SUMMARY OF THE INVENTION

The present invention has been completed in order to achieve the above objects and provides a process for modifying the surface of an inorganic biomaterial, which comprises treating an inorganic biomaterial containing at least CaO and $P_2O_5$ with an aqueous solution containing calcium ion and/or phosphate ion to precipitate a calcium phosphate crystal on the surface of the biomaterial.

DETAILED DESCRIPTION OF THE INVENTION

Figure 1:
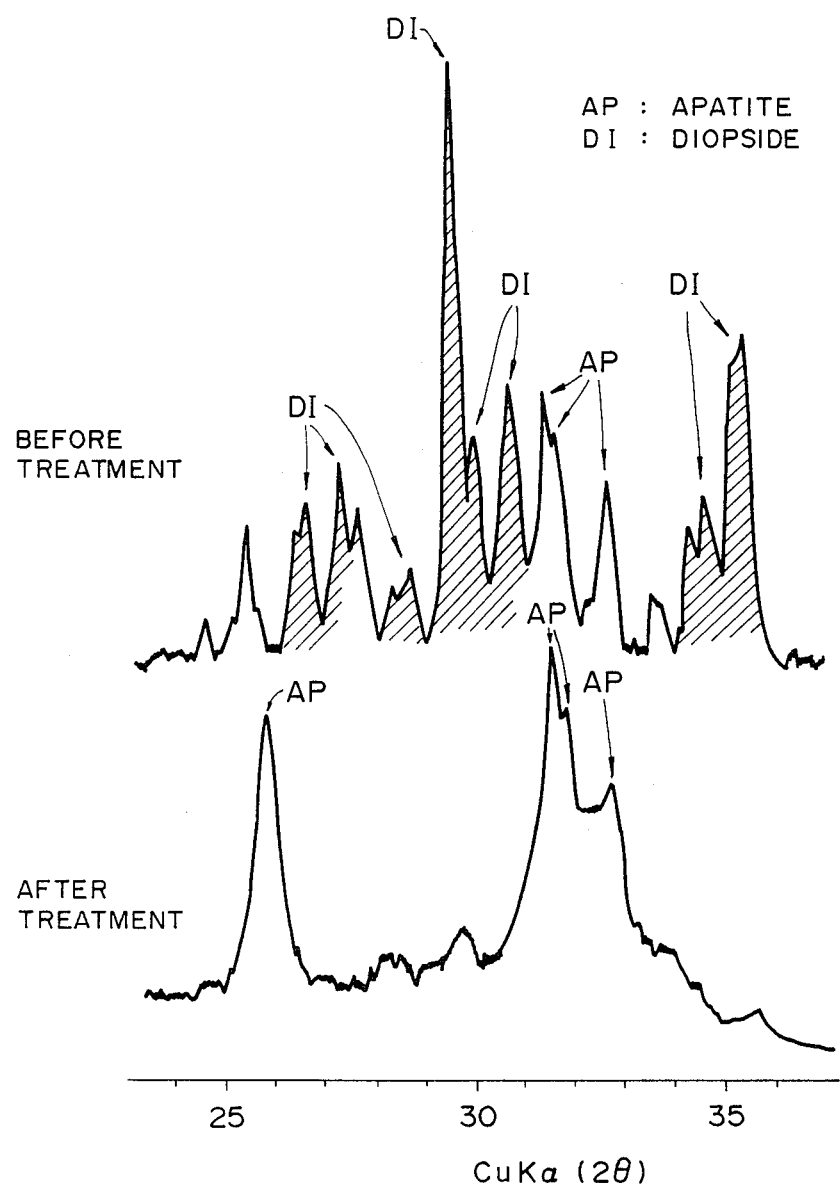
FIG. 1 shows the X-ray diffraction patterns of a crystallized glass before and after surface treatment.

The present invention is explained in detail below.

In the process of the present invention, the aqueous solution containing calcium ion and/or phosphate ion, used for the surface treatment of an inorganic biomaterial containing at least CaO and $P_2O_5$ is obtained by dissolving in water a water-soluble calcium salt [e.g. $CaCO_3$, $CaO$, $CaCl_2$, $CaF_2$, $Ca(NO_3)_2$, $Ca(COO)_2$, $Ca(CH_3COO)_2$, $Ca[CH_3CH(OH)COO]_2$] and/or a phosphoric acid salt [e.g. $H_3PO_4$, $(NH_4)_2HPO_4$, $NH_4H_2PO_4$, $(NH_4)_3PO_4$, $KH_2PO_4$, $K_2HPO_4$, $Na_2HPO_4$, $NaH_2PO_4$].

When an inorganic biomaterial containing at least CaO and $P_2O_5$ is immersed in the above aqueous solution containing calcium ion and/or phosphate ion, at least either of the CaO and the $P_2O_5$ at the surface of the biomaterial dissolves in the aqueous solution in the form of calcium ion or phosphate ion and reacts with the phosphate ion or the calcium ion in the aqueous solution, whereby a calcium phosphate crystal is precipitated on the surface of the inorganic biomaterial. The size and the amount of the crystal precipitated varies depending upon the temperature and time of the above treatment. The calcium phosphate crystal formed on the inorganic biomaterial is fine at a treatment temperature of 10°–50° C. At a treatment temperature of 50°–100° C., the crystal is slightly larger but the treatment time can be relatively short. When the treatment temperature is over 100° C., the aqueous solution boils, making the treatment of the inorganic biomaterial difficult; however, it is still possible to form a calcium phosphate crystal. When the treatment temperature exceeds 200° C., the dissolution rate of the calcium ion and the phosphate ion from the inorganic biomaterial is too high, making it difficult to obtain a calcium phosphate crystal on the surface of the inorganic biomaterial. Accordingly, the treatment temperature is preferably 10°–200° C.

While the treatment time differs by the type of the inorganic material, a short treatment time makes small the amount of the calcium phosphate crystal precipitated and too long a treatment time makes the crystal coarse. In order to obtain a calcium phosphate crystal of appropriate size (0.1–5 μm), a treatment time of about 1–240 hours is preferred although the time differs by the treatment temperature employed.

The type of the calcium phosphate crystal obtained differs by the pH of the aqueous solution used. Brushite ($CaHPO_4.2H_2O$) is formed from an aqueous solution having a pH of less than 4; at least one crystal of brushite, octacalcium phosphate [$Ca_8H_2(PO_4)_6.5H_2O$] and hydroxyapatite [$Ca_{10}(PO_4)_6(OH)_2$] is precipitated from an aqueous solution of pH 4–5; and hydroxyapatite is formed from an aqueous solution having a pH of more than 5. When a large amount of carbonic acid is present in the aqueous solution, the hydroxyapatite crystal obtained contains the carbonate ion in some cases. It is preferable that biomaterials have hydroxyapatite on the surfaces because the hydroxyapatite composition is substantially same as the inorganic components of bones. Therefore, the use of an aqueous solution having a pH higher than 5 is preferable. The pH of the aqueous solution can be adjusted using an aqueous solution of an acid or alkali such as HCl, NaOH, $NH_4OH$, $Ca(OH)_2$ or the like.

The treatment temperature and time are determined by subjecting the surface of the inorganic biomaterial during treatment to X-ray diffractometry, infrared reflection spectrum measurement, Raman spectrum measurement and observation by scanning electron microscope.

The reason for formation of a calcium phosphate crystal on the surface of the inorganic biomaterial is that the inorganic biomaterial contains at least CaO and $P_2O_5$ and that at least either of them dissolves in the aqueous solution in the form of calcium ion and/or phosphate ion and reacts with the phosphate ion and/or calcium ion in the aqueous solution. The bioactive crystallized glass or the ceramic-bioactive crystallized glass composite can suitably be subjected to surface modification according to the process of the present invention because the CaO and $P_2O_5$ contained in the crystallized glass or the composite is soluble in an aqueous solution containing calcium ion and/or phosphate ion.

In the present process, the crystallized glass used as an inorganic biomaterial is preferably a bioactive crystallized glass comprising the following components of the following proportions

| | |
|---|---|
| CaO | 12–56% by weight |
| $P_2O_5$ | 1–27% by weight |
| $SiO_2$ | 22–50% by weight |
| MgO | 0–34% by weight |
| $Al_2O_3$ | 0–25% by weight | in a total amount of at least 90% by weight. This crystallized glass contains an apatite crystal, at least one alkaline earth metal silicate crystal selected from wollastonite, diopside, forsterite, akermanite, anorthite, etc., and further in some cases, a β-tricalcium phosphate crystal [β-$Ca_3(PO_4)_2$].

Also in the present process, the ceramic-crystallized glass composite used as an inorganic biomaterial is preferably a ceramic-bioactive crystallized glass composite obtained by dispersing a reinforcing ceramic selected from zirconia, alumina and a zirconia-alumina ceramic in the above crystallized glass in an amount of 5–50% by volume based on the resulting composite.

The bioactive crystallized glass, or the bioactive crystallized glass used as a matrix in the ceramic-bioactive crystallized glass composite has a compositional restriction as mentioned above. The reason is described below.

When the CaO content is less than 12%, the glass powder has very poor sinterability, making it impossible to obtain a crystallized glass of high strength. When the content is more than 56%, the resulting glass has a high tendency of devitrification. Accordingly, the CaO content is restricted to fall within a range of 12 to 56%, preferably 23 to 50%. When the $P_2O_5$ content is less than 1%, the resulting glass has a high tendency of devitrification. When the content is more than 27%, the total amount of the precipitated crystals of alkaline earth metal silicates such as wollastonite, diopside, forsterite, akermanite, anorthite and the like is small. Therefore, the $P_2O_5$ content is restricted to 1 to 27%, preferably 1 to 22%. When the $SiO_2$ content is less than 22%, the glass powder has poor sinterability and the total amount of the precipitated crystals of alkaline earth metal silicates is small. When the content is more than 50%, the resulting glass tends to be devitrified. Hence, the $SiO_2$ content is restricted to 22 to 50%, preferably 25 to 50%. MgO is not an essential component but when it is contained, an apatite crystal is formed in too small an amount, if the content is more than 34%. Therefore, the MgO content is restricted to 34% or below, preferably 15% or below. $Al_2O_3$ is not an essential component, either. However, when it is contained, an apatite crystal is formed in too small an amount, if the content is more than 25%. Therefore, the $Al_2O_3$ content is restricted to 25% or below, preferably 17% or below.

The bioactive crystallized glass can comprise, in addition to the above five components, at least one component selected from $K_2O$, $Li_2O$, $Na_2O$, $TiO_2$, $ZrO_2$, SrO, $Nb_2O_5$, $Ta_2O_5$, $B_2O_3$, $F_2$ and $Y_2O_3$ (all of which give no harm to human bodies) in a total amount of 10% or less. When the total content of these optional components is more than 10%, the amounts of apatite crystal and alkaline earth metal silicate crystal(s) formed decrease in some cases. Therefore, the content of the above optional components is preferably 10% or less. When the $F_2$ content is more than 5%, the resulting glass is easily devitrified. When the $Y_2O_3$ content is more than 5%, the amounts of apatite crystal and alkaline earth metal silicate crystal(s) formed decrease. Accordingly, the $F_2$ content and the $Y_2O_3$ content are each restricted to 5% or below.

A glass powder having the above composition is sintered and crystallized, whereby a bioactive crystallized glass for use in the present process is obtained. Also, a glass powder having the above composition is mixed with 5–50% by volume, based on the resulting mixture, of a reinforcing ceramic of powder or fiber form, such as zirconia, alumina, zirconia-alumina ceramic or the like, and the mixture is sintered and crystallized, whereby a ceramic-bioactive crystallized glass composite for use in the present process is obtained. The reason for restricting the proportion of the reinforcing ceramic to 5–50% by volume is that when the proportion is less than 5% by volume, the resulting composite has substantially no improvement in mechanical strength over the matrix glass and, when the proportion is more than 50% by volume, the resulting composite has poor densification and has substantially no improvement in mechanical strength over the matrix glass. When the proportion is 5–50% by volume, no such problems exist.

When these inorganic biomaterials containing CaO and $P_2O_5$ are immersed in an aqueous solution, the CaO and $P_2O_5$ slightly dissolve therein. Therefore, it is possible to precipitate a calcium phosphate crystal on the surfaces of these inorganic biomaterials according to the present process. Depending upon the treating conditions (treatment time and treatment temperature) employed, it is possible to cover the ceramic portion of the surfaces of the ceramic-crystallized glass composite completely with the calcium phosphate crystal precipitated.

The present invention is explained in more detail below by referring to Examples.

Example 1

(Corresponds to Nos. 1 to 32 of Table 1.)

A material batch for a glass having a composition as shown in Table 1 was prepared from an oxide, a carbonate, a phosphate, a hydrate, a fluoride, etc. The material batch was placed in a platinum crucible and melted at 1,450°–1,500° C. for 2 hours. The resulting melt was poured into water and, after drying, ground to particle sizes of 20 μm or less in a ball mill. The thus obtained glass powder was press-molded at a pressure of 1,000 kg/cm$^2$. The resulting molding was heated from room temperature to 1,150° C. at a rate of 3° C./min and kept at 1,150° C. for 2 hours in an electric furnace to give rise to sintering and crystallization. Then the molding was cooled to room temperature in the furnace to obtain a crystallized glass.

A test piece of 15 mm×20 mm×2 mm was prepared by cutting the above crystallized glass and then polished at the surface with a No. 1,000 alumina powder. The test piece was then surface-treated under conditions as shown in Table 1. The surface of the thus treated test piece was observed by a scanning electron microscope, which showed the formation of a product on the entire surface of the test piece. This product was confirmed by the X-ray diffraction and Raman spectrum to be a calcium phosphate crystal as shown in Table 1. This matter is explained on the case of No. 2 of Table 1. FIG. 1 shows the X-ray diffraction patterns before and after surface treatment, of the No. 2 material of Table 1. According to FIG. 1, when the crystallized glass having an apatite crystal and a diopside crystal as crystaline phases was treated according to the present process, the diopside peak became too small to confirm the presence of diopside, and the apatite peak became very large. This indicates that the entire surface of the crystallized glass was covered with apatite.

TABLE 1

| | Material No. | | | |
|---|---|---|---|---|
| | 1 | 2 | 3 | 4 |
| Crystallized glass used for treatment | | | | |
| Glass composition (wt. %) | | | | |
| CaO | 44.7 | 36.3 | 26.8 | 24.6 |
| P$_2$O$_5$ | 16.3 | 16.3 | 14.1 | 16.0 |
| SiO$_2$ | 34.2 | 35.4 | 34.1 | 28.7 |
| Others | MgO 4.6 | MgO 11.5 | MgO 11.5 | MgO 30.7 |
| | F$_2$ 0.2 | F$_2$ 0.5 | Al$_2$O$_3$ 12.7 | |
| | | | F$_2$ 0.8 | |
| Crystalline phases precipitated in the crystallized glass | Apatite Wollastonite Diopside | Apatite Diopside | Apatite Anorthite Diopside Forsterite β-Tricalcium phosphate | Apatite Forsterite Diopside β-Tricalcium phosphate |
| Treatment conditions | | | | |
| Source of calcium ion and/or phosphate ion | H$_3$PO$_4$ | H$_3$PO$_4$ | CaCO$_3$ | Ca(CH$_3$COO)$_2$ + H$_3$PO$_4$ |
| Concentration in solution (%) | 5 | 5 | 5 | 5 (total) |
| PH | 7.2 | 8.7 | 4.5 | 7.5 |
| Reagent used for pH adjustment | Ca(OH)$_2$ | NaOH | HCl | NH$_4$OH |
| Treatment temperature (°C.) | 37 | 37 | 80 | 80 |
| Treatment time (hour) | 120 | 240 | 48 | 48 |
| Product formed on surface | Hydroxyapatite | Hydroxyapatite | Brushite Octacalcium phosphate Hydroxyapatite | Hydroxyapatite |

| | 5 | 6 | 7 | 8 |
|---|---|---|---|---|
| Crystallized glass used for treatment | | | | |
| Glass composition (wt. %) | | | | |
| CaO | 26.1 | 16.6 | 47.4 | 47.4 |
| P$_2$O$_5$ | 23.0 | 16.2 | 6.2 | 6.2 |
| SiO$_2$ | 29.8 | 37.2 | 42.2 | 42.2 |
| Others | MgO 18.6 | MgO 29.5 | Y$_2$O$_3$ 2.0 | MgO 2.0 |
| | F$_2$ 0.5 | F$_2$ 0.5 | ZrO$_2$ 2.0 | Ta$_2$O$_5$ 2.0 |
| | Li$_2$O 2.0 | | F$_2$ 0.2 | F$_2$ 0.2 |
| Crystalline phases precipitated in the crystallized glass | Apatite Akermanite Diopside β-Tricalcium phosphate | Apatite Diopside Forsterite | Apatite Wollastonite | Apatite Wollastonite |
| Treatment conditions | | | | |
| Source of calcium ion and/or phosphate ion | Ca(COO)$_2$ | CaO + CaF$_2$ + CaCl$_2$ | H$_3$PO$_4$ | H$_3$PO$_4$ |
| Concentration in solution (%) | 5 | 5 (total) | 20 | 20 |
| PH | 3.8 | 4.2 | 7.4 | 7.4 |
| Reagent used for pH adjustment | HCl | HCl | NH$_4$OH | NH$_4$OH |
| Treatment temperature (°C.) | 80 | 80 | 95 | 95 |
| Treatment time (hour) | 48 | 48 | 48 | 48 |
| Product formed on surface | Brushite | Brushite Octacalcium phosphate | Hydroxyapatite | Hydroxyapatite |

TABLE 1-continued

|  | 9 | 10 | 11 | 12 |
|---|---|---|---|---|
| Crystallized glass used for treatment | | | | |
| composition (wt. %) | | | | |
| CaO | 48.3 | 47.9 | 48.3 | 48.3 |
| $P_2O_5$ | 6.3 | 6.3 | 6.3 | 6.3 |
| $SiO_2$ | 43.2 | 42.6 | 43.2 | 43.2 |
| Others | $F_2$ 0.2 | $F_2$ 0.2 | $F_2$ 0.2 | $F_2$ 0.2 |
|  | $TiO_2$ 2.0 | $K_2O$ 3.0 | SrO 2.0 | $Nb_2O_5$ 2.0 |
| Crystalline phases precipitated | Apatite | Apatite | Apatite | Apatite |
| in the crystallized glass | Wollastonite | Wollastonite | Wollastonite | Wollastonite |
| Treatment conditions | | | | |
| Source of calcium ion and/or phosphate ion | $H_3PO_4$ | $CaCl_2$ + $KH_2PO_4$ | $H_3PO_4$ |  |
| Concentration in solution (%) | 20 | 10 (total) | 20 | 20 |
| PH | 7.4 | 7.0 | 7.2 | 7.2 |
| Reagent used for pH adjustment | $NH_4OH$ | $NH_4OH$ | $NH_4OH$ | $NH_4OH$ |
| Treatment temperature (°C.) | 95 | 95 | 95 | 95 |
| Treatment time (hour) | 48 | 48 | 48 | 48 |
| Product formed on surface | Hydroxyapatite | Hydroxyapatite | Hydroxyapatite | Hydroxyapatite |

|  | 13 | 14 | 15 | 16 |
|---|---|---|---|---|
| Crystallized glass used for treatment | | | | |
| Glass composition (wt. %) | | | | |
| CaO | 48.3 | 48.3 | 23.2 | 49.2 |
| $P_2O_5$ | 6.3 | 6.3 | 27.0 | 1.0 |
| $SiO_2$ | 43.2 | 43.2 | 49.8 | 49.8 |
| Others | $F_2$ 0.2 | $F_2$ 0.2 | | |
|  | $Na_2O$ 2.0 | $B_2O_3$ 2.0 | | |
| Crystalline phases precipitated | Apatite | Apatite | Apatite | Apatite |
| in the crystallized glass | Wollastonite | Wollastonite | Wollastonite | Wollastonite |
|  | | | β-Tricalcium | |
|  | | | phosphate | |
| Treatment conditions | | | | |
| Source of calcium ion and/or phospate ion | $Ca(NO_3)_2$ + $H_3PO_4$ | $H_3PO_4$ | $Ca[CH_3CH(OH)COO]_2$ | $(NH_4)_2HPO_4$ |
| Concentration in solution (%) | 10 (total) | 20 | 20 | 20 |
| PH | 8.0 | 7.8 | 8.2 | 8.0 |
| Reagent used for pH adjustment | $NH_4OH$ | $NH_4OH$ | NaOH | Not used |
| Treatment temperature (°C. | 95 | 95 | 95 | 120 |
| Treatment time (hour) | 48 | 48 | 48 | 24 |
| Product formed on surface | Hydroxyapatite | Hydroxyapatite | Hydroxyapatite | Hydroxyapatite |

|  | 17 | 18 | 19 | 20 |
|---|---|---|---|---|
| Crystallized glass used for treatment | | | | |
| Glass composition (wt. %) | | | | |
| CaO | 47.5 | 55.6 | 49.3 | 47.8 |
| $P_2O_5$ | 14.0 | 22.0 | 6.5 | 6.5 |
| $SiO_2$ | 38.5 | 22.4 | 44.0 | 44.0 |
| Others | | | $F_2$ 0.2 | MgO 1.5 |
|  | | | | $F_2$ 0.5 |
| Crystalline phases precipitated | Apatite | Apatite | Apatite | Apatite |
| in the crystallized glass | Wollastonite | Wollastonite | Wollastonite | Wollastonite |
| Treatment conditions | | | | |
| Source of calcium ion and/or phosphate ion | $(NH_4)_2HPO_4$ | $(NH_4)_2HPO_4$ | $(NH_4)_2HPO_4$ | $(NH_4)_2HPO_4$ |
| Concentration in solution (%) | 20 | 20 | 20 | 5 |
| PH | 7.4 | 7.4 | 7.4 | 7.3 |
| Reagent used for pH adjustment | Not used | Not used | Not used | Not used |
| Treatment temperature (°C.) | 120 | 120 | 200 | 50 |
| Treatment time (hour) | 24 | 24 | 1 | 120 |
| Product formed on surface | Hydroxyapatite | Hydroxyapatite | Hydroxyapaptite | Hydroxyapatite |

|  | 21 | 22 | 23 | 24 |
|---|---|---|---|---|
| Crystallized glass used for treatment | | | | |
| Glass composition (wt. %) | | | | |
| CaO | 12.0 | 45.0 | 45.0 | 45.0 |
| $P_2O_5$ | 15.5 | 6.0 | 6.0 | 6.0 |
| $SiO_2$ | 47.7 | 39.0 | 39.0 | 39.0 |
| Others | $Al_2O_3$ 24.8 | $K_2O$ 9.5 | $Li_2O$ 9.5 | $Na_2O$ 9.5 |
| Crystalline phases precipitated | Apatite | Apatite | Apatite | Apatite |
| in the crystallized glass | Anorthite | Wollastonite | Wollastonite | Wollastonite |
|  | β-Tricalcium | β-Tricalcium | β-Tricalcium | β-Tricalcium |
|  | phosphate | phosphate | phosphate | phosphate |
| Treatment conditions | | | | |
| Source of calcium ion and/or phosphate ion | $Ca(NO_3)_2$ + $NaH_2PO_4$ | $K_2HPO_4$ | $(NH_4)_2HPO_4$ | $Na_2HPO_4$ |
| Concentration in solution (%) | 5 (total) | 5 | 5 | 5 |
| PH | 8.2 | 8.0 | 7.6 | 7.5 |
| Reagent used for pH adjustment | Not used | Not used | Not used | Not used |

TABLE 1-continued

|  |  |  |  |  |
|---|---|---|---|---|
| Treatment temperature (°C.) | 100 | 100 | 95 | 95 |
| Treatment time (hour) | 48 | 48 | 48 | 48 |
| Product formed on surface | Hydroxyapatite | Hydroxyapatite | Hydroxyapatite | Hydroxyapatite |

|  | 25 | 26 | 27 | 28 |
|---|---|---|---|---|
| Crystallized glass used for treatment |  |  |  |  |
| Glass composition (wt. %) |  |  |  |  |
| CaO | 45.0 | 45.0 | 45.0 | 45.0 |
| $P_2O_5$ | 6.0 | 6.0 | 6.0 | 6.0 |
| $SiO_2$ | 39.0 | 39.0 | 39.0 | 39.0 |
| Others | $TiO_2$ 9.5 | $ZrO_2$ 9.5 | SrO 9.5 | $Nb_2O_5$ 9.5 |
|  | $F_2$ 0.5 | $F_2$ 0.5 | $F_2$ 0.5 | $F_2$ 0.5 |
| Crystalline phases precipitated in the crystallized glass | Apatite Wollastonite $\beta$-Tricalcium phosphate | Apatite Wollastonite $\beta$-Tricalcium phosphate | Apatite Wollastonite $\beta$-Tricalcium phosphate | Apatite Wollastonite $\beta$-Tricalcium phosphate |
| Treatment conditions |  |  |  |  |
| Source of calcium ion and/or phospate ion | $(NH_4)_2HPO_4$ | $(NH_4)_2HPO_4$ | $(NH_4)_2HPO_4$ | $(NH_4)_2HPO_4$ |
| Concentration in solution (%) | 5 | 5 | 5 | 5 |
| PH | 7.5 | 7.5 | 7.2 | 7.5 |
| Reagent used for pH adjustment | Not used | Not used | Not used | Not used |
| Treatment temperature (°C.) | 95 | 95 | 95 | 95 |
| Treatment time (hour) | 48 | 48 | 48 | 48 |
| Product formed on surface | Hydroxyapatite | Hydroxyapatite | Hydroxyapatite | Hydroxyapatite |

|  | 29 | 30 | 31 | 32 |
|---|---|---|---|---|
| Crystallized glass used for treatment |  |  |  |  |
| Glass composition (wt. %) |  |  |  |  |
| CaO | 45.0 | 45.0 | 45.0 | 45.0 |
| $P_2O_5$ | 6.0 | 6.0 | 6.0 | 6.0 |
| $SiO_2$ | 39.0 | 39.0 | 44.5 | 44.0 |
| Others | $Ta_2O_5$ 9.5 | $B_2O_3$ 9.5 | $F_2$ 4.5 | $Y_2O_3$ 5.0 |
|  | $F_2$ 0.5 | $F_2$ 0.5 |  |  |
| Crystalline phases precipitated in the crystallized glass | Apatite Wollastonite $\beta$-Tricalcium phosphate | Apatite Wollastonite $\beta$-Tricalcium phosphate | Apatite Wollastonite $\beta$-Tricalcium phosphate | Apatite Wollastonite $\beta$-Tricalcium phosphate |
| Treatment conditions |  |  |  |  |
| Source of calcium ion and/or phoshpate ion | $(NH_4)_2HPO_4$ | $(NH_4)_2HPO_4$ | $NH_4H_2PO_4$ | $(NH_4)_3PO_4$ |
| Concentration in solution (%) | 5 | 5 | 5 | 5 |
| PH | 7.4 | 7.4 | 7.4 | 7.6 |
| Reagent used for pH adjustment | Not used | Not used | Not used | Not used |
| Treatment temperature (°C.) | 95 | 95 | 95 | 95 |
| Treatment time (hour) | 48 | 48 | 48 | 48 |
| Product formed on surface | Hydroxyapatite | Hydroxyapatite | Hydroxyapatite | Hydroxyapatite |

Example 2

(Corresponds to Nos. 1 to 21 of Table 2).

A material batch for a glass having a composition as shown in Table 2 was prepared from an oxide, a carbonate, a phosphate, a hydrate, a fluoride, etc. The material batch was placed in a platinum crucible and melted at 1,450°–1,550° C. for 2 hours. The resulting melt was poured into water and, after drying, ground to particle size of 20 μm or less in a ball mill. The obtained glass powder was mixed with a zirconia powder, a zirconia fiber, an alumina powder, an alumina fiber (all of these were commercially available), or a zirconai-alumina ceramic powder (which was obtained by calcinating a mixture of a tetragonal zirconia powder and an α-alumina powder) in proportions as shown in Table 2. The mixture was wet-blended for several hours in a ball mill and dried. The dried mixture placed in a graphite mold was heated from room temperature to 1,150° C. at a constant rate of 3° C./min in a furnace while applying a pressure of 300 kg/cm² and kept at 1,150° C. for 2 hours to give rise to sintering and crystallization. Then, the resulting molding was cooled to room temperature in the furnace to obtain a ceramic-crystallized glass composite.

Figure 2:
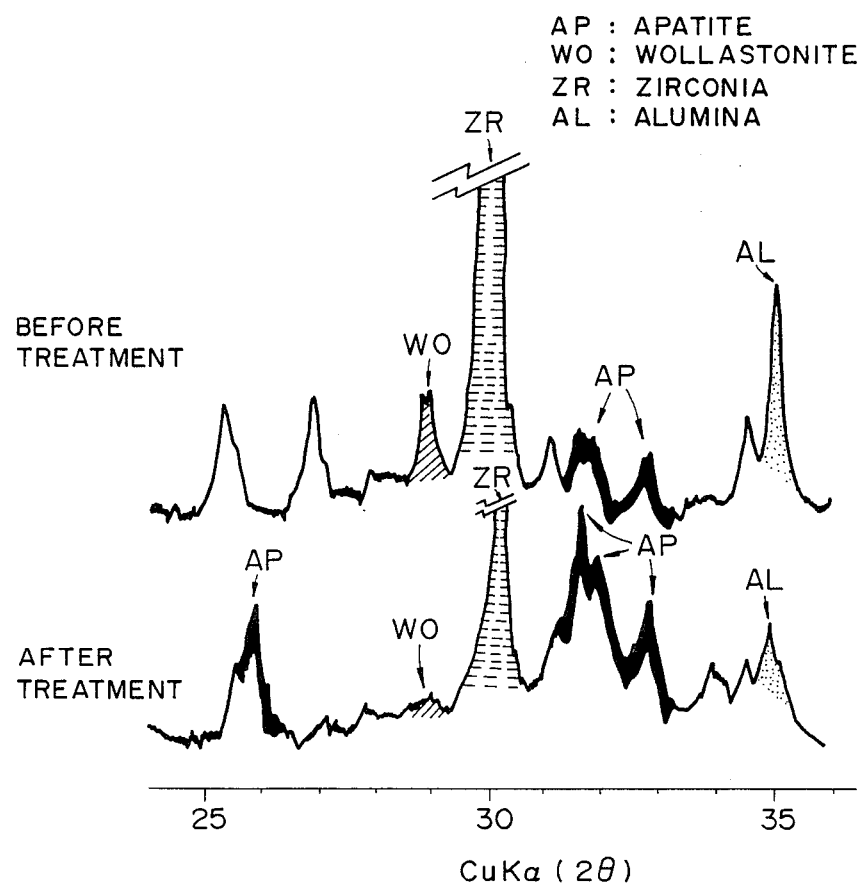
FIG. 2 shows the X-ray diffraction patterns of a ceramic-crystallized glass composite before and after surface treatment.

A test piece of 15 mm×20 mm×2 mm was prepared by cutting the above ceramic-crystallized glass composite and then polished at the surface with a No. 1,000 alumina powder. The test piece was then surface-treated under conditions as shown in Table 2. The surface of the thus treated test piece was observed by a scanning electron microscope. The observation showed that a product was formed not only on the surface of the matrix glass (the crystallized glass) but also on the surface of the ceramic and that the entire surface of the ceramic-crystallized glass composite was covered with the product. The product was confirmed by the X-ray diffraction pattern and Raman spectrum to be a calcium phosphate crystal as shown in Table 2. This matter is explained on the case of No. 9 of Table 2. FIG. 2 shows the X-ray diffraction patterns before and after treatment, of the No. 9 mateiral of Table 2. According to FIG. 2, when the ceramic-crystallized glass composite obtained by dispersing a zirconia-alumina powder as a reinforcing ceramic in a crystallized glass having an apatite crystal and a wollastonite crystal as crystalline phases was treated according to the present process, the peaks of wollastonite, zirconia and alumina became small and the peak of apatite became large. This indicates that apatite was precipitated on the entire surface of the ceramic-crstallized glass composite.

With respect to the bending strengths before and after surface treatment, the No. 2 material showed 3,000 kg/cm² before treatment and 3,200 kg/cm² after treatment; the No. 3 showed 3,000 kg/cm² before treatment and 3,000 kg/cm² after treatment; the No. 7 material showed 3,300 kg/cm² before treatment and 3,100 kg/cm₂ after treatment; the No. 9 material showed 3,800 kg/cm² before treatment and 3,800 kg/cm² after treatment; and the No. 10 material showed 3,100 kg/cm² before treatment and 3,000 kg/cm² after treatment. Thus, any of these materials showed no significant reduction in bending strength by treatment, while some material showed slight increase in bending strength by treatment. Similarly, any of other materials of Table 2 showed no significant reduction in bending strength by treatment.

TABLE 2

| | Material No. | | | |
|---|---|---|---|---|
| | 1 | 2 | 3 | 4 |
| Ceramic-crystallized glass composite used for treatment | | | | |
| Crystallized glass as a matrix | | | | |
| Composition (wt %) | | | | |
| CaO | 12.0 | 47.8 | 36.3 | 40.0 |
| $P_2O_5$ | 15.5 | 6.5 | 16.3 | 15.5 |
| $SiO_2$ | 47.7 | 44.0 | 35.4 | 28.0 |
| Others | $Al_2O_3$ 24.8 | MgO 1.5 $F_2$ 0.2 | MgO 11.5 $F_2$ 0.5 | MgO 12.0 $F_2$ 0.5 $ZrO_2$ 4.0 |
| Crystalline phases precipitated in the crystallized glass | Apatite Anorthite β-Tricalcium phosphate | Apatite Wollastonite | Apatite Diopside | Apatite Diopside Akermanite Forsterite |
| Reforcing ceramic | | | | |
| Type of ceramic | Zirconia powder | Zirconia powder | Zirconia powder | Zirconia powder |
| Amount used (vol. % in composite) | 20 | 20 | 20 | 20 |
| Treatment conditions | | | | |
| Source of calcium ion and/or phosphate ion | $Ca(NO_3)_2 + H_3PO_4$ | $(NH_4)_2HPO_4$ | $(NH_4)_2HPO_4$ | $(NH_4)_2HPO_4$ |
| Concentration in solution (%) | 10 (total) | 20 | 20 | 20 |
| PH | 8.0 | 8.0 | 8.0 | 7.3 |
| Reagent for pH adjustment | $NH_4OH$ | Not used | Not used | Not used |
| Treatment temperature (°C.) | 90 | 90 | 90 | 90 |
| Treatment time (hour) | 48 | 48 | 48 | 48 |
| Product formed on surface | Hydroxyapatite | Hydroxyapatite | Hydroxyapatite | Hydroxyapatite |

| | 5 | 6 | 7 | 8 |
|---|---|---|---|---|
| Ceramic-crystallized glass composite used for treatment | | | | |
| Crystallized glass as a matrix | | | | |
| Composition (wt. %) | | | | |
| CaO | 24.6 | 47.8 | 47.8 | 47.8 |
| $P_2O_5$ | 16.0 | 6.5 | 6.5 | 6.5 |
| $SiO_2$ | 28.7 | 44.0 | 44.0 | 44.0 |
| Others | MgO 30.7 | Mgo 1.5 $F_2$ 0.2 | MgO 1.5 $F_2$ 0.2 | MgO 1.5 $F_2$ 0.2 |
| Crystalline phases precipitated in the crystallized glass | Apatite Forsterite Diopside β-Tricalcium phosphate | Apatite Wollastonite | Apatite Wollastonite | Apatite Wollastonite |
| Reinforcing ceramic | | | | |
| Type of ceramic | Zirconia powder | Zirconia fiber | Alumina powder | Alumina fiber |
| Amount used (vol. % in composite) | 20 | 20 | 20 | 20 |
| Treatment conditions | | | | |
| Source of calcium ion and/or phosphate ion | $Ca(CH_3COO)_2 + H_3PO_4$ | $(NH_4)_2HPO_4$ | $(NH_4)_2HPO_4$ | $(NH_4)_2HPO_4$ |
| Concentration in solution (%) | 5 (total) | 5 | 5 | 5 |
| PH | 7.5 | 7.3 | 7.3 | 7.3 |
| Reagent for pH adjustment | $NH_4OH$ | Not used | Not used | Not used |
| Treatment temperature (°C.) | 80 | 95 | 95 | 95 |
| Treatment time (hour) | 48 | 48 | 48 | 48 |
| Product formed on surface | Hydroxyapatite | Hydroxyapatite | Hydroxyapatite | Hydroxyapatite |

| | 9 | 10 | 11 | 12 |
|---|---|---|---|---|
| Ceramic-crystallized glass composite used for treatment | | | | |
| Crystallized glass as a matrix | | | | |
| Composition (wt. %) | | | | |
| CaO | 47.8 | 47.8 | 47.8 | 47.8 |
| $P_2O_5$ | 6.5 | 6.5 | 6.5 | 6.5 |
| $SiO_2$ | 44.0 | 44.0 | 44.0 | 44.0 |
| Others | MgO 1.5 $F_2$ 0.2 | MgO 1.5 $F_2$ 0.2 | MgO 1.5 $F_2$ 0.2 | MgO 1.5 $F_2$ 0.2 |
| Crystalline phases precipitated | Apatite | Apatite | Apatite | Apatite |

TABLE 2-continued

| | Material No. | | | |
|---|---|---|---|---|
| in the crystallized glass | Wollastonite | Wollastonite | Wollastonite | Wollastonite |
| Reinforcing ceramic | | | | |
| Type of ceramic | Zirconia-alumina powder (ZrO$_2$:Al$_2$O$_3$ = 80:20 wt. %) | Zirconia-alumina powder (ZrO$_2$:Al$_2$O$_3$ = 60:40 wt. %) | Zirconia-alumina powder (ZrO$_2$:Al$_2$O$_3$ = 20:80 wt. %) | Zirconia powder |
| Amount used (vol. % in composite) | 20 | 20 | 20 | 35 |
| Treatment conditions | | | | |
| Source of calcium ion and/or phosphate ion | (NH$_4$)$_2$HPO$_4$ | (NH$_4$)$_2$HPO$_4$ | (NH$_4$)$_2$HPO$_4$ | (NH$_4$)$_2$HPO$_4$ |
| Concentration in solution (%) | 5 | 5 | 5 | 5 |
| PH | 7.3 | 7.3 | 7.3 | 7.3 |
| Reagent for pH adjustment | Not used | Not used | Not used | Not used |
| Treatment temperature (°C.) | 95 | 95 | 95 | 95 |
| Treatment time (hour) | 48 | 48 | 48 | 48 |
| Product formed on surface | Hydroxyapatite | Hydroxyapatite | Hydroxyapatite | Hydroxyapatite |
| | 13 | 14 | 15 | 16 |
| Ceramic-crystallized glass composite used for treatment | | | | |
| Crystallized glass as a matrix | | | | |
| Composition (wt. %) | | | | |
| CaO | 47.8 | 26.1 | 16.6 | 47.8 |
| P$_2$O$_5$ | 6.5 | 23.0 | 16.2 | 6.5 |
| SiO$_2$ | 44.0 | 29.8 | 37.2 | 44.0 |
| Others | MgO 1.5 F$_2$ 0.2 | MgO 18.6 F$_2$ 0.5 | MgO 29.5 F$_2$ 0.5 | MgO 1.5 F$_2$ 0.2 |
| Crystalline phases precipitated in the crystallized glass | Apatite Wollastonite | Apatite Akermanite Diopside β-Tricalcium phosphate | Apatite Diopside | Apatite Wollastonite |
| Reinforcing ceramic | | | | |
| Type of ceramic | Zirconia powder | Zirconia powder | Zirconia powder | Zirconia powder |
| Amount used (vol. % in composite) | 50 | 20 | 20 | 20 |
| Treatment conditions | | | | |
| Source of calcium ion and/or phosphate ion | (NH$_4$)$_2$HPO$_4$ | Ca(NO$_3$)$_2$ | CaCl$_2$ | (NH$_4$)$_2$HPO$_4$ |
| Concentration in solution (%) | 5 | 5 | 5 | 5 |
| PH | 7.3 | 3.7 | 4.2 | 7.3 |
| Reagent for pH adjustment | Not used | HCl | HCl | Not used |
| Treatment temperature (°C.) | 95 | 80 | 80 | 37 |
| Treatment time (hour) | 48 | 48 | 48 | 240 |
| Product formed on surface | Hydroxyapatite | Brushite | Brushite Octacalcium phosphate | Hydroxyapatite |
| | 17 | 18 | 19 | 20 |
| Ceramic-crystallized glass composite used for treatment | | | | |
| Crystallized glass as a matrix | | | | |
| Composition (wt. %) | | | | |
| CaO | 47.8 | 47.8 | 47.7 | 36.3 |
| P$_2$O$_5$ | 6.5 | 6.5 | 6.5 | 16.3 |
| SiO$_2$ | 44.0 | 44.0 | 44.0 | 35.4 |
| Others | MgO 1.5 F$_2$ 0.2 | MgO 1.5 F$_2$ 0.2 | MgO 1.5 F$_2$ 0.3 | MgO 11.5 F$_2$ 0.5 |
| Crystalline phases precipitated in the crystallized glass | Apatite Wollastonite | Apatite Wollastonite | Apatite Wollastonite | Apatite Diopside |
| Reinforcing ceramic | | | | |
| Type of ceramic | Zirconia powder | Zirconia powder | Zirconia powder | Zirconia powder |
| Amount used (vol. % in composite) | 20 | 20 | 5 | 10 |
| Treatment conditions | | | | |
| Source of calcium ion and/or phosphate ion | (NH$_4$)$_2$HPO$_4$ | (NH$_4$)$_2$HPO$_4$ | H$_3$PO$_4$ | H$_3$PO$_4$ |
| Concentration in solution (%) | 5 | 5 | 5 | 5 |
| PH | 7.3 | 7.3 | 7.5 | 7.6 |
| Reagent for pH adjustment | Not used | Not used | NaOH | NaOH |
| Treatment temperature (°C.) | 150 | 200 | 90 | 90 |
| Treatment time (hour) | 5 | 1 | 48 | 48 |
| Product formed on surface | Hydroxyapatite | Hydroxyapatite | Hydroxyapatite | Hydroxyapatite |
| | | | | 21 |
| Ceramic-crystallized glass composite used for treatment | | | | |
| Crystallized glass as a matrix | | | | |
| Composition (wt. %) | | | | |
| CaO | | | | 47.7 |
| P$_2$O$_5$ | | | | 6.5 |

TABLE 2-continued

| | Material No. |
|---|---|
| SiO$_2$ | 44.0 |
| Others | MgO 1.5 |
| | F$_2$ 0.3 |
| Crystalline phases precipitated in the crystallized glass | Apatite Wollastonite |
| Reinforcing ceramic | |
| Type of ceramic | Zirconia-alumina powder (ZrO$_2$:Al$_2$O$_3$ = 60:40 wt. %) |
| Amount used (vol. % in composite) | 40 |
| Treatment conditions | |
| Source of calcium ion and/or phosphate ion | (NH$_4$)$_2$HPO$_4$ |
| Concentration in solution (%) | 5 |
| PH | 7.3 |
| Reagent for pH adjustment | Not used |
| Treatment temperature (°C.) | 90 |
| Treatment time (hour) | 48 |
| Product formed on surface | Hydroxyapatite |

As described in detail above, according to the present process for modifying the surface of a biomaterial, there can be precipitated on the surface of a biomaterial a calcium phosphate crystal which is necessary for the biomaterial to form a chemical bonding with human bones. Therefore, the bioactivity of a biomaterial for use as an artificial bone or a dental implant can be improved by the present process.

What is claimed is:

1. A process for modifying the surface of a bioactive ceramic-crystallized-glass-composite biomaterial, which comprises providing said biomaterial, as a biomaterial which contains a crystallized glass of at least 12-56% CaO, 1-27% P$_2$O$_5$ and 22-50% SiO$_2$ and a reinforcing amount of a reinforcing ceramic of zirconia and/or alumina ceramic dispersed in the crystallized glass, contacting said biomaterial with an aqueous solution containing calcium ion and/or phosphate ion to dissolve CaO and/or P$_2$O$_5$ from said biomaterial into said solution and precipitate a calcium phosphate crystal on the surface of said biomaterial, said contacting being effected for sufficient time and temperature to improve bioactivity of the biomaterial and to completely cover the composite biomaterial with calcium phosphate crystal, and removing said composite biomaterial from the aqueous solution as a calcium-phosphate-covered biomaterial with increased bioactivity.

2. A process according to claim 1, wherein the composite is a ceramic-bioactive crystallized glass composite obtained by dispersing a reinforcing ceramic selected from zirconia, alumina and zirconia-alumina ceramic in a bioactive crystallized glass comprising the following components of the following proportions

| CaO | 12-56% by weight |
|---|---|
| P$_2$O$_5$ | 1-27% by weight |
| SiO$_2$ | 22-50% by weight |
| MgO | 0-34% by weight |
| Al$_2$O$_3$ | 0-25% by weight | in a total content of at least 90% by weight and having an apatite crystal and at least one alkaline earth metal silicate crystal selected from the group consisting of wollastonite, diopside, forsterite, akermanite and anorthite, precipitated therein.

3. A process according to claim 2, wherein the amount of a reinforcing ceramic dispersed in a bioactive crystallized glass is 5-50% by volume based on the composite.

4. A process according to claim 1, wherein the aqueous solution has a pH of 5 or more.

5. A process according to claim 1, wherein the temperature of the aqueous solution is from 10° to 200° C.

6. A process according to claim 1, wherein the treatment is conducted for 1-240 hours.

* * * * *